US006838429B2

(12) United States Patent
Paslin

(10) Patent No.: US 6,838,429 B2
(45) Date of Patent: Jan. 4, 2005

(54) ATOPIC DERMATITIS TREATMENT METHOD

(76) Inventor: David A. Paslin, PMB #24, 205 DeAnza Blvd., San Mateo, CA (US) 94402

( * ) Notice: Subject to any disclaimer, the term of this patent is extended or adjusted under 35 U.S.C. 154(b) by 359 days.

(21) Appl. No.: 09/920,897

(22) Filed: Aug. 1, 2001

(65) Prior Publication Data

US 2002/0009489 A1 Jan. 24, 2002

Related U.S. Application Data

(63) Continuation of application No. 09/624,748, filed on Jul. 24, 2000, now abandoned, which is a continuation of application No. 09/426,093, filed on Oct. 22, 1999, now abandoned.

(51) Int. Cl.[7] .............................................. A01N 37/18
(52) U.S. Cl. ................................ 514/2; 514/2; 514/12; 424/450; 604/19; 604/20; 604/290; 607/49; 530/350; 530/300
(58) Field of Search ....................... 514/2, 12; 424/450; 604/20, 19, 290; 607/49; 530/350, 300

(56) References Cited

U.S. PATENT DOCUMENTS 5,573,503 A * 11/1996 Untereker et al. ............ 604/20
5,733,269 A * 3/1998 Fuisz .......................... 604/290

FOREIGN PATENT DOCUMENTS

| WO | WO 99/09178 | 2/1999 |
| WO | WO 99/34818 | 7/1999 |

OTHER PUBLICATIONS

Krathwohl et al., PNAS, vol. 94, pp. 9875–9880, 1997.*

* cited by examiner

Primary Examiner—Karen Cochrane Carlson
Assistant Examiner—Hope A. Robinson
(74) Attorney, Agent, or Firm—Wilson Sonsini Goodrich & Rosati

(57) ABSTRACT

Compositions are provided for treating atopic dermatitis, other atopic diseases and other inflammatory or allergic skin disorders. The compositions include proteins from Molluscum Contagiosum Virus (MCV), or fragments, variants, analogs, and derivatives thereof which exhibit AD inhibiting activity. Examples of MCV proteins which exhibit AD inhibiting activity include MC148P1, MC148P2, MC148P3, other MC148P type proteins, and fragments, variants, analogs, and derivatives of MC148P1, MC148P2, MC148P3, and other MC148P type proteins which possess AD inhibiting activity. The fragments, variants, analogs and derivatives may be less than 100% homologous to MCV proteins so long as they are sufficiently homologous such that AD inhibiting activity is preserved.

20 Claims, 7 Drawing Sheets

SEQ. ID. No. 1

MCV Type 1

ORF 148R (166,992 – 167,303)

1    ATGAGGGGCGGAGACGTCTTCGCGAGCGTTGTCTTGATGCTGTTACTTGC

51   ACTACCGCGACCGGGAGTGTCACTCGCGAGACGGAAATGTTGTTTGAATC

101  CCACAAATCGTCCGATCCCGAATCCTTTACTGCAAGATCTATCACGCGTC

151  GACTATCAGGCGATAGGACATGACTGCGGACGGGAAGCTTTCAGAGTGAC

201  GCTGCAAGACGGAAGACAAGGCTGCGTTAGCGTTGGTAACAAGAGCTTAC

251  TAGACTGGCTTCGGGGACACAAGGATCTCTGCCCTCAGATATGGTCCGGG

301  TGCGAGTCTCTGTAA

Figure 1A

SEQ.ID.No.2

MC148R1 Protein

```
                                    Active        Site
                                    |              |
1    MRGGDVFASVVLMLLL . ALPRPGVS . . . . . . LARRKCCLNPT       35
                                            |
                                            Hypothetical Receptor
                                            Binding Site Absent Chemokine
                            Activation Site
```

36   NRPIPNPLLQDLSRVDYQAIGHDCGREAFRVTLQD                       70

71   GRQGCVSVGNKSLLDWLRGHKDLCPQIWSGCESL                        104

Figure 1B

SEQ. ID. No. 3

MCV Type 2

ORF 148R (166,992 - 167,303)

1   ATGAGGGCCAGAGCCGTCTTCGCGAGCGTTGTCTTGACGCTGTTACTTGC

51  ACTACCGCGACCGGGAGTGTCACTCTCGAGACGGAAATGTTGTTTGAATC

101 CTACAAATCGTCCGATACCGAGGCCTTTACTGCAAGATCTAGACAAAGTC

151 GATTATCAGCCGATGGGACATGACTGCGGACGGGAAGCTTTCAGAGTGAC

201 GCTGCAAGACGGAAGACAAGGCTGTGTTAGCGTTGGTAACCAGAGTTTAC

251 TAGACTGGCTGAAGGGACACAAGGATCTCTGCCCGCGGATGTGGCCCGGG

301 TGCGAGTCTCTGTAA

Figure 2A

SEQ. ID. No. 4

MC148R2  Protein

```
                              Active      Site
                              |           |
1   MRARAVFASVVLTLLL . ALPRPGVS . . . . . . . LSRRKCCLNPT   35
                                     |
                                     | Hypothetical Receptor
                                     | Binding Site
                                     |
                              Absent Chemokine
                              Activation Site

36  NRPIPRPLLQDLDKVDYQPMGHDCGREAFRVTLQD                    70

71  GRQGCVSVGNQSLLDWLKGHKDLCPRMWPGCESL                    104
```

Figure 2B

SEQ. ID. No. 5

MCV 148R from Index Case shown for nucleotides 20 to 312
reading in direction from 5' to 3'

| | | |
|---|---|---|
| 21 | CGCGAGCGTTGTCTTGATGCTGTTACTTGCACTACCGCGA | 60 |
| 61 | CCGGGAGTGTCACTCGCGAGACGGAAATGTTGTTTGAATC | 100 |
| 101 | CCACAAATCGTCCGATCCCGAATCCTTTACTGCAAGATCT | 140 |
| 141 | ATCACGCGTCGACTATCAGGCGATAGGACATGACTGCGGA | 180 |
| 181 | CGGGAAGCTTTCAGAGTGACGCTGCAAGACGGAAGACAAG | 220 |
| 221 | GCTGCGTTAGCGTTGGTAACAAGAGCTTACTAGACTGGCT | 260 |
| 261 | TCGGGGACACAAGGATCTCTGCCCTCAGATATGGTCCGGG | 300 |
| 301 | TGCGAGTCTCTG | |

Figure 3

SEQUENCE LISTING

<160> NUMBER OF SEQ ID NOS: 5

<210> SEQ ID NO 1
<211> LENGTH: 315
<212> TYPE: DNA
<213> ORGANISM: Molluscum contagiosum virus

<400> SEQUENCE: 1
atgaggggcg agacgtctt cgcgagcgtt gtcttgatgc tgttacttgc actaccgcga      60
ccgggagtgt cactcgcgag acggaaatgt tgtttgaatc ccacaaatcg tccgatcccg     120
aatcctttac tgcaagatct atcacgcgtc gactatcagg cgataggaca tgactgcgga    180
cgggaagctt tcagagtgac gctgcaagac ggaagacaag gctgcgttag cgttggtaac    240
aagagcttac tagactggct tcggggacac aaggatctct gccctcagat atggtccggg    300
tgcgagtctc tgtaa                                                    315

<210> SEQ ID NO 2
<211> LENGTH: 104
<212> TYPE: PRT
<213> ORGANISM: Molluscum contagiosum virus

<400> SEQUENCE: 2

Met Arg Gly Gly Asp Val Phe Ala Ser Val Val Leu Met Leu Leu Leu
 1               5                  10                  15

Ala Leu Pro Arg Pro Gly Val Ser Leu Ala Arg Arg Lys Cys Cys Leu
                20                  25                  30

Asn Pro Thr Asn Arg Pro Ile Pro Asn Pro Leu Leu Gln Asp Leu Ser
            35                  40                  45

Arg Val Asp Tyr Gln Ala Ile Gly His Asp Cys Gly Arg Glu Ala Phe
        50                  55                  60

Arg Val Thr Leu Gln Asp Gly Arg Gln Gly Cys Val Ser Val Gly Asn
 65                  70                  75                  80

Lys Ser Leu Leu Asp Trp Leu Arg Gly His Lys Asp Leu Cys Pro Gln
                85                  90                  95

Ile Trp Ser Gly Cys Glu Ser Leu
            100

<210> SEQ ID NO 3
<211> LENGTH: 315
<212> TYPE: DNA
<213> ORGANISM: Molluscum contagiosum virus

<400> SEQUENCE: 3
atgagggcca gagccgtctt cgcgagcgtt gtcttgacgc tgttacttgc actaccgcga     60
ccgggagtgt cactctcgag acggaaatgt tgtttgaatc ctacaaatcg tccgataccg    120
aggcctttac tgcaagatct agacaaagtc gattatcagc cgatgggaca tgactgcgga    180
cgggaagctt tcagagtgac gctgcaagac ggaagacaag gctgtgttag cgttggtaac    240
cagagtttac tagactggct gaagggacac aaggatctct gcccgcggat gtggcccggg    300
tgcgagtctc tgtaa                                                    315

<210> SEQ ID NO 4
<211> LENGTH: 104
<212> TYPE: PRT
<213> ORGANISM: Molluscum contagiosum virus -continued

```
<400> SEQUENCE: 4

Met Arg Ala Arg Ala Val Phe Ala Ser Val Val Leu Thr Leu Leu Leu
 1               5                  10                  15

Ala Leu Pro Arg Pro Gly Val Ser Leu Ser Arg Arg Lys Cys Cys Leu
            20                  25                  30

Asn Pro Thr Asn Arg Pro Ile Pro Arg Pro Leu Leu Gln Asp Leu Asp
        35                  40                  45

Lys Val Asp Tyr Gln Pro Met Gly His Asp Cys Gly Arg Glu Ala Phe
    50                  55                  60

Arg Val Thr Leu Gln Asp Gly Arg Gln Gly Cys Val Ser Val Gly Asn
65                  70                  75                  80

Gln Ser Leu Leu Asp Trp Leu Lys Gly His Lys Asp Leu Cys Pro Arg
                85                  90                  95

Met Trp Pro Gly Cys Glu Ser Leu
            100

<210> SEQ ID NO 5
<211> LENGTH: 295
<212> TYPE: DNA
<213> ORGANISM: Molluscum contagiosum virus

<400> SEQUENCE: 5
cgcgagcgtt gtcttgatgc tgttacttgc actaccgcga ccgggagtgt cactcgcgag      60
acggaaatgt tgtttgaatc ccacaaatcg tccgatcccg aatcctttac tgcaagatct     120
atcacgcgtc gactatcagg cgataggaca tgactgcgga cgggaagctt tcagagtgac     180
gctgcaagac ggaagacaag gctgcgttag cgttggtaac aagagcttac tagactggct     240
tcggggacac aaggatctct gccctcagat atggtccggg tgcgagtctc tgtaa          295
```

ATOPIC DERMATITIS TREATMENT METHOD

RELATIONSHIP TO CO-PENDING APPLICATIONS

This application is a continuation of U.S. application Ser. No. 09/624,748, filed Jul. 24, 2000, now abandoned which is a continuation of U.S. application Ser. No. 09/426,093, filed Oct. 22, 1999, abandoned which is incorporated herein by reference in its entirety.

BACKGROUND OF THE INVENTION

1. Field of the Invention

The present invention relates to the treatment of inflammatory and/or allergic skin disorders and more particularly to the treatment of Atopic Dermatitis using compositions which include a protein derived from Molluscum Contagiosum Virus (MCV).

2. Description of Related Art

Atopic Dermatitis (AD) is a genetically determined, reaginically (IgE) associated, chronic disease of the skin affecting approximately 8 million adults and children in the United States. In AD, the skin is dry, easily irritated, subject to immediate hypersensitivity type of allergic responses, typically scaly, often thickened, commonly red, frequently infected, sometimes exudative and above all itchy. Among adults with AD, coexisting respiratory allergy (allergic rhinitis and/or asthma), has been reported to range from 63% to 85%.

Reaginic diseases, i.e. atopic diseases, are characterized by the capacity to form IgE antibodies, on a genetic basis, resulting in immediate hypersensitivity reactions upon exposure to many specific allergens, most prominent among which may be the house dust mite (*Dermatophagoides pteronyssinus*), but which also include pollens, molds and danders. Multiple genetic factors contribute to expression of this phenotype. Atopic susceptibility genes include those making several major histocompatibility complex (HLA) class II molecules, IL-4 receptor proteins and IgE high affinity receptor proteins. An atopy susceptibility gene recently identified involves a guanine for adenine substitution at nucleotide 1902 of the IL-4 receptor gene, synthesizing the α subunit of the IL-4 receptor on the surface of B lymphocytes which results in an arginine for glutamine substitution at peptide position 576 (R576). This substitution was found in 57% of patients with AD, but in only 17% of non-atopic controls, p=0.001. A majority of subjects identified as carrying a single copy of the mutant allele had atopy, suggesting a dominant effect, yet penetrance is modified by other factors, since others carrying allele R576 lacked atopy. R576 alters the binding profile of the adjacent phosphorylated tyrosine residue, which impairs enzyme mediated termination of signaling of cytokine receptors, causing sustained or exaggerated receptor signaling. (NEJM 337:172–5, 1997).

The frequent chronic infections that occur on the skin of AD patients appears to result both from the defective barrier of AD skin and from an impaired immune response, e.g. upon testing with trichopyton antigen, patients with AD show immediate rather than the normal delayed immune response. The most common of the microbes infecting AD skin is *Staphylococcus aureus* (Staph). In AD skin, Staph induces and exacerbates itching, increases inflammation and provokes oozing and eczematization. Of those who ooze, 100% will culture out Staph. Of those who don't, the majority will still culture out Staph, though less massively. About 50% of patients with AD produce IgE directed against Staph toxins. Viruses, too, more readily grow in AD skin than in normal skin, including herpes, wart and molluscum viruses.

There is no known cure for AD. The many treatment approaches attest the inadequacy and limitations of each. In briefest outline, these treatments include avoidance of soap and water, hydrating the skin, dietary restrictions, avoidance of irritants and allergens in the environment, tars, antihistamines, hyposensitization, corticosteroids, antibacterials, antifungals, ultraviolet light, leukotriene blockers, inhibitors of mast cell content release, evening primrose oil, Chinese herbal teas, pentoxifylline, azathioprine, cyclosporin A, cyclophosphamide, tacrolimus, interferon γ, thymopentin and phosphodiesterase inhibitors. The corticosteroids are most commonly used in clinical practice, but suffer from incomplete responses, tachyphylaxis, induction of atrophy and the potential of suppression of the pituitary-adrenal axis if used widely enough, long enough and potently enough.

SUMMARY OF THE INVENTION

The invention relates to compositions for treating atopic dermatitis (AD), other atopic diseases (including asthma, allergic rhinitis, hives) and other inflammatory and/or allergic disorders of the skin. The compositions according to the present invention include proteins from Molluscum Contagiosum Virus (MCV), or fragments, variants, analogs, and derivatives thereof which exhibit AD inhibiting activity. Examples of MCV proteins which exhibit AD inhibiting activity include MC148P1, MC148P2, MC148P3, other MC148P type proteins, and fragments, variants, analogs, and derivatives of MC148P1, MC148P2, MC148P3, and other MC148P type proteins which possess AD inhibiting activity. The fragments, variants, analogs and derivatives may be less than 100% homologous to MC148P1, MC148P2, MC184P3 so long as they are sufficiently homologous such that AD inhibiting activity is preserved. Collectively, the above MCV proteins, fragments, variants, analogs and derivatives are referred to herein as MC 148 proteins (MC 148P).

In one embodiment, the composition is suitable for topical application to a portion of patient's skin which exhibits AD signs and/or symptoms. In another embodiment, the composition is adapted for delivery by other routes including by injection intravenously, intramuscularly, subcutaneously or intradermally or by electroporation or iontophoresis. The composition may be delivered systemically or it may be delivered remotely or locally at or near a portion of patient's skin which exhibits AD signs and/or symptoms.

The invention also relates to a method for treating AD as well as other atopic diseases and other inflammatory or allergic skin disorders (see above) which includes administering a composition according to the present invention to patients with AD, other atopic diseases and other inflammatory or allergic skin disorders.

The invention also relates to a kit which includes a composition according to the present invention. The kit may optionally include multiple separately packaged portions of the composition, where each portion is in an amount suitable for a single administration or for multiple administrations, e.g. administration from a tube or ajar. The kit may also optionally include instructions regarding the administration of the composition to a patient having AD, other atopic diseases and other inflammatory or allergic skin disorders. In one of many variations, the instructions may teach how locally to administer the composition to the patient.

BRIEF DESCRIPTION OF THE FIGURES

FIG. 1A illustrates the DNA sequence (SEQ. ID. No. 1) of MCV type 1, ORF 148 R.

FIG. 1B illustrates the amino acid sequence (SEQ. ID. No. 2) of the protein produced from the DNA sequence of MCV type 1, ORF 148 R, illustrated in FIG. 1A.

FIG. 2A illustrates the DNA sequence (SEQ. ID. No. 3) of MCV type 2, ORF 148 R.

FIG. 2B illustrates the amino acid sequence of the protein produced from the DNA sequence (SEQ. ID. No. 4) of MCV type 2, ORF 148 R, illustrated in FIG. 2A.

FIG. 3 illustrates the DNA sequence (SEQ. ID. No. 5) of MCV ORF 148 R from the index case—the DNA of which is identical to that of MCV type 1, ORF 148 R, shown for nucleotides 20 to 312.

DETAILED DESCRIPTION

Figure 4A:
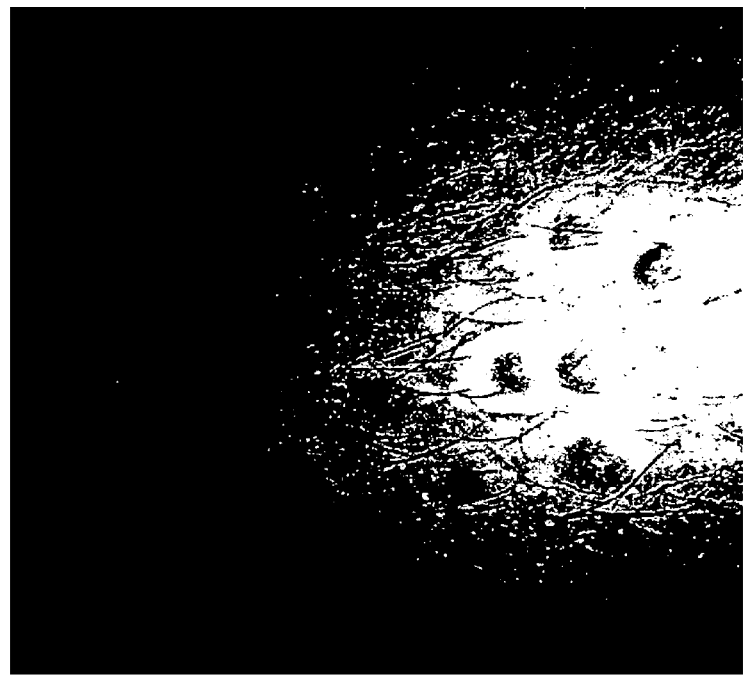
FIG. 4A illustrates the clinically demonstrable inhibitory effect of MCV upon a field of AD at a focal distance of 6 inches.

The compositions of the present invention include MC148 proteins which exhibit AD inhibiting activity. As noted above, these proteins may be MCV proteins which exhibit AD inhibiting activity such as MC148P1, MC148P2, MC148P3, as well as fragments, variants, analogs, and derivatives of MCV proteins which exhibit AD inhibiting activity. The fragments, variants, analogs and derivatives may be less than 100% homologous to an MCV protein so long as they are sufficiently homologous such that AD inhibiting activity is preserved.

Molluscum Contagiosum Virus (MCV) is a large DNA virus of the Pox family. MCV causes small, harmless lesions in the skin of infected persons. These small bumps (papules) resemble pimples that typically appear domed and shiny and that usually show a small central pit. MCV can be spread from person to person by direct skin contact and by fomites. It is harmless and possesses no cancerous potential.

MC148P1 is natively produced by MCV type 1. MC148P2 is natively produced by MCV type 2.

The Applicant has observed in his clinical practice of medicine the inhibitory effect of MCV upon AD. The inhibitory effect endured at least 3 years, i.e. for the duration of the MCV infection, any clinical side effect and without tachyphylaxis. By viewing micrographs at focal distances of 6 inches (FIG. 4A} and of 2 inches (FIG. 4B) one sees a field of AD manifest as mildly scaly, somewhat lichenified reddish brown skin. Clear zones of clinically normal skin surround each papule of MCV. The zone of inhibition around each MCV papule may be viewed as analogous to the zone of inhibition around a penicillin disk on an agar plate streaked with Streptococci. The therapeutic implications are also analogous.

FIG. 5A shows a photomicrograph of a biopsy taken at the edge of and immediately adjacent to a papule of MCV. The edge of the papule is seen on the lower left of the panel. The top of the panel shows the base of the epidermis. A paucity of mononuclear cells is seen around small blood vessels of the superficial dermal plexus. The lack of inflammation in the dermis adjacent to the MCV papule resembles the appearance of the dermis in normal, i.e. non-AD skin. By contrast, FIG. 5B shows a photomicrograph of a biopsy taken concurrently from a similar area of AD on the same patient but remote from any MCV papule. The moderately dense, predominantly lymphohistocytic infiltrate admixed with eosinophils is seen not only around the blood vessels of the superficial plexus, but also around vessels of the papillae and those of the upper reticular dermis. The inflammatory cells extend into the interstitium.

Applicant interprets the above observations to show that MCV produces a protein that inhibits the signs and symptoms of AD. This protein is believed to be MC148P1. Published work indicates that MC148P2 and other MC148 proteins to share the same or similar anti-inflammatory properties. (Krathwohl et al. in Proc Nat'l Acad Sci 94: 9875–9880; Buget, J. J. et al. in Virology 242: 51–59, 1998; Damon, I. et al. in Proc Nat'l Acad Sci 95:6403–6407, 1998.)

Standard type 1 MCV is the major type of MCV found in nature and consists of 190,289 base pairs. This comprises the entire genome, excepting covalently closed terminal hairpin loops. This genome was deposited in Gen Bank (accession number U60315) as described in Senkevich et al. "Genome Sequence of a Human Tumorigenic Poxvirus: Prediction of Specific Host Response-Evasion Genes", Science 273:813–816, 1996. MCV type 1 includes a DNA sequence of 312 bases, identified as ORF 148R, that encode a protein 104 amino acids in length referred to herein as MC148P1. Synthesis, characterization and effects of MC148P (MC148P1) are discussed in Damon et al. "Broad Spectrum Chemokine Antagonistic Activity of a Human Poxvirus Chemokine Homolog", Proc. Nat'l. Acad. Sci. USA, 95:6403–6407, 1998 and in Krathwohl et al "Functional Characterization of the C—C Chemokine-like Molecules Encoded by Molluscum Contagiosum Virus Types 1 and 2", Proc. Natl. Acad. Sci. USA 94:9875–9880, 1997.

The DNA sequence of MCV148 type 1 (SEQ ID NO:1) is illustrated in FIG. 1A and the amino acid sequence of MC148P1 (denoted as MC148P by Damon et al and as MC 148R1 Protein by Krathwohl et al) (SEQ ID NO:2) is provided in FIG. 1B.

MC 148P2 (also denoted MC148R 2 Protein), produced by MCV type 2, is a variant of MC148P1. MC148P2 is also 104 amino acids in length. The DNA sequence for MCV type 2 (SEQ ID NO:3) is illustrated in FIG. 2A and the amino acid sequence of MC148P2 (SEQ ID NO:4) is illustrated in FIG. 2B. The DNA sequence for MC148R2 has been deposited in Gen Bank (Accession number U96749) by Krathwohl et al, as referenced above.

The MC148R2 has 89% homology to MC148R1. Amino acid sequences of MC148R2 Protein (MC148P2) showed 87% homology with those of MC148R1 Protein (MC148P1) for complete sequences and 86% homology when the putative leader sequence was removed. From the NH2 terminus, the leader sequences of MC148P1 and MC148P2 consist of 24 amino acids of which 20 amino acids share identical positions. The chemokine activation domain, found between positions 24 and 25 of MC148P1 and MC148P2, is absent in both. The 5 amino acids of positions 25–29, comprising the hypothetical receptor binding site, are identical except at position 26 where MC148P2 bears a serine substitution for the alanine residue found in most isolates of MC148P1. This substitution at position 26 does not appear to affect the inhibitory activity of either type of MC148P. The leucine at position 47 from the amino terminus, correlated with the ability of MC148P to inhibit neutrophil chemotaxis, is conserved in MC148P1 and MC148P2.

Further, the amino acid sequences of MC148P1 and MC148P2 share significant homology with CC (β) chemokines such as Macrophage Inflammatory Protein-1α(MIP-1α) (Krathwohl et al, see above) and CC (β) chemokines including MIP-1α, RANTES, Macrophage Chemotactic Proteins-1 and -3 (MCP-1 and MCP-3) (Damon et al, see above). The amino acid sequences of MC148P1 and of MC148P2 also share significant homology with CXC (α) chemokines SDF-1 for the attraction of monocytes and lymphocytes and IL-8 for the attraction of neutrophils. MC148P1 and MC148P2 share the identical positions of the 4 canonical cysteine residues with the above mentioned CC and the CXC chemokines at positions 30, 31, 59 and 75 of the respective amino acid chains. Taken together, these structural homologies may best account for the capacity of MC148P to inhibit the chemotaxis of human peripheral blood mononuclear cells (Krathwohl et al) and of monocytes, lymphocytes and neutrophils (Damon et al). The inhibition results from the direct binding of MC148P to chemokine receptors (Damon et al).

1. Compositions According to the Present Invention

The invention relates to compositions adapted for the treatment of Atopic Dermatitis (AD), other atopic diseases and other inflammatory or allergic skin disorders. These compositions comprise a protein or sequence of amino acids selected from the group consisting of: MC148P1, MC148P2, MC148P3, another MC148P type protein, and a fragment, variant, analog, or derivative of these proteins which possesses AD inhibiting activity.

A. Fragments of MC148P

Fragments of MC148P may be any amino acid sequence which is sufficiently homologous to a MC148P that AD inhibiting activity is preserved. These fragments may be generated by genetic engineering of translation stop sites within the coding region (discussed below). Alternatively, treatment of the MC148P with proteolytic enzymes, known as proteases, can produce a variety of N-terminal, C-terminal and internal fragments. Examples of fragments may include contiguous portions of an MC148P of 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more amino acids in length. These fragments may have primary, secondary (β-sheets, α-sheets, or other), tertiary and quaternary structures, including domains and loops.

These fragments may be purified according to known methods, such as precipitation (e.g. ammonium sulfate), HPLC, ion exchange chromatography, affinity chromatography (including immunoaffinity chromatography) or various size separations (sedimentation, gel electrophoresis, gel filtration).

B. Variants of MC148P

Variants of MC148P for inclusion in the compositions of the present invention can be substitutional, insertional or deletion variants of MC148P. Deletion variants lack one or more residues of the native protein which are not essential for function or immunogenic activity, and are exemplified by the variants lacking a leader sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without loss of other functions or properties. Substitutions of this kind preferably are conservative, that is, one amino acid is replaced with another of similar shape and charge. Conservative substitutions are well known in the art and include, for example, the changes of: alanine to serine; arginine to lysine; asparagine to glutamine or histidine; aspartate to glutamate; cysteine or threonine to serine; glutamate to aspartate; glycine or leucine to proline; histidine to asparagine, lysine or glutamine; isoleucine to leucine or valine; leucine to valine; lysine to arginine; tyrosine to phenylalanine or tryptophan; the reverse of the above changes; other substitutions.

The following is a discussion based upon changing of the amino acids of a protein to create an equivalent, or even an improved, second-generation molecule. For example, certain amino acids may be substituted for other amino acids in a protein structure without appreciable loss of interactive binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those withic are within ±1 are particularly preferred, and those within ±0.5 even more particularly preferred.

The substitution of like amino acids can be made effectively on the basis of hydrophilicity. U.S. Pat. No. 4,554, 101, incorporated herein by reference, states that the greatest local average hydrophilicity of a protein, as governed by the hydrophilicity of its adjacent amino acids, correlates with a biological property of the protein. As detailed in U.S. Pat.

No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within +/−2 is preferred, those that are within +/−1 are particularly preferred, and those within +/−0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al. Eds., Chapman and Hall, N.Y. (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of MCV-type 1, type 2 and other type viral proteins, but with altered and even improved characteristics.

A specialized kind of insertional variant is the fusion protein. This molecule generally has all or a substantial portion of the native molecule, linked at the N- or C-terminus, to all or a portion of a second polypeptide.

For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

The above proteins, fragments and/or variants for use in the compositions of the present invention can be produced by recombinant expression means or, if small enough, generated by an automated peptide synthesizer.

C. Administration to a Patient

Compositions according to the present invention, for the treatment of AD, other atopic diseases and other inflammatory or allergic skin disorders may include one or more pharmaceutically acceptable carriers to provide a pharmaceutically acceptable composition for delivery to a patient. The phrase "pharmaceutically or pharmacologically acceptable" refers to molecular entities and compositions that are unlikely to produce adverse, allergic or other untoward reactions when administered to an animal or a human patient. As used herein, "pharmaceutically acceptable carrier" includes any and all solvents, suspensions, dispersion media, coatings, oils antibacterial and antifungal agents, preservatives, detergents, emollients, astringents, ointments, creams, lotions, gels; occlusion techniques; iontophoresis, electroporation or other devices, isotonic and absorption delaying agents and the like, including the types of carriers referenced in Smith E W & Maibach H I: "Percutaneous Penetration Enhancers", CRC Press, 1995, N.W. Boca Raton, Fla. Methods contemplated for delivery of the composition are not limited to chemical penetration enhances, but also include non-chemical methods such as iontophoresis and electroporation. Preferred pharmaceutically acceptable carriers include sulfoxides such as decylmethylsulfoxide, pyrrolidones and combinations of these (Azone), macromolecular microspheres and liposomes. Supplementary active ingredients also can be incorporated into the compositions. The use of such carriers and penetration enhancers for pharmaceutically active ingredients is well known in the art.

The pharmaceutically acceptable compositions of the present invention may include any classical or nonclassical pharmaceutical preparation which includes an MC148P or a fragment, variant, analog or derivative of a MC148P as an active ingredient. Administration of these compositions according to the present invention will be via any common route so long as the target tissue is available via that route. Because the treatment of skin disease is contemplated, the route is preferably adapted for the treatment of skin, e.g. a localized delivery, optionally topically or via subcutaneous injection. Iontophoresis, electroporation or other techniques can be used for administration of the pharmaceutically acceptable composition.

When the composition is delivered topically, the composition is preferably applied directly to the area affected by the skin disease. For subcutaneously or other administration, the most desirable point of delivery need not necessarily be at or near the area affected by the skin disease.

The pharmaceutically acceptable compositions according to the present invention may include sterile aqueous solutions or dispersions or suspensions for the extemporaneous preparation of sterile injectable solutions or dispersions. The form should be sterile and should be fluid in embodiments where the fluid is to be delivered by injection. The form should be stable under the conditions of manufacture and storage and should be preserved against the contaminating action of microorganisms, such as bacteria and fungi. The carrier can be a solvent or dispersion medium containing, e.g. water, ethanol, polyol (such as glycerol, propylene glycol, liquid polyethylene glycol and the like), suitable mixtures thereof, and vegetable or other oils. Proper fluidity can be maintained, by way of example, by the use of a coating, such as lecithin, by the maintenance of the required particle size in the case of dispersion and by the use of surfactants. The prevention of the action of microorganisms can be brought about by various antibacterial and antifungal agents, e.g. parabens, chlorobutanol, phenol, sorbic acid, thimerosal, benzalkonium and the like. In many cases, it may be preferable to include isotonic agents, e.g. sugars or sodium chloride. Prolonged absorption of the injectable compositions can be brought about by the use in the compositions of agents delaying absorption, e.g. aluminum monostearate and gelatin.

Sterile injectable solutions may be prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention may be formulated in a neutral or salt form. Pharmaceutically acceptable salts include acid addition salts (formed with the free amino groups of the protein) which are generally formed with inorganic acids such as, e.g. hydrochloric or phosphoric acids, or organic acids such as acetic, oxalic, tartaric, mandelic and the like. Salts formed with free carboxyl groups can also be derived from inorganic bases such as, e.g. sodium, potassium, ammonium, calcium, or ferric hydroxides, and such organic bases as isopropylamine, trimethylamine, histidine, procaine and the like.

Upon formulation, solutions may be administered in a manner compatible with the dosage formulation and in such amount as is therapeutically effective. The formulations are easily administered in a variety of dosage forms such as injectable solutions, and the like. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 ml of isotonic NaCl solution and either added to 1000 ml of hypodermo-clysis fluid or injected at the proposed site of infusion (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics Standards.

2. Descriptions of FIGS. 4A–5B

Figure 4B:
FIG. 4B illustrates the clinically demonstrable inhibitory effect of MCV upon field of AD at a focal distance of 2 inches.

FIGS. 4A–4B illustrate the clinically demonstrable inhibitory effect of MCV upon a field of AD.

In FIGS. 4A and 4B the patient (PR) is a light skinned African American man, 16 years of age at the time these photos were taken. PR has had a chronic, widespread, waxing and waning atopic dermatitis. He has carried a persistent and heavy infection of Molluscum contagiosum virus (MCV). The numerous light reddish tan, mildly lucent, sometimes umbilicated hillocks shown on the clinical photos are papules of epidermis infected with MCV. Many of the papules are 5 mm in diameter (range 3 to 7 mm).

FIG. 4A photograph was taken at a focal distance of 6 inches and FIG. 4B photograph at 2 inches. FIG. 4A shows a background of atopic dermatitis manifest as mildly scaly, somewhat lichenified, reddish brown skin. Clear zones of clinically normal skin surround each papule of MCV. The clear zones range from 3 to 8 mm in dimension from the edge of a MCV papule to the edge of the background dermatitis. There appears to be a rough correlation between the size of a MCV papule and the width of the clear zone around it. The lack of a direct linear correlation could be associated with colonization of the skin with *Staphylococcus aureus*. *S. aureus* frequently colonizes the skin of patients with atopic dermatitis and almost invariably exacerbates the dermatitis. PR has proven *S. aureus* skin infections.

FIG. 4B includes a photograph is taken of an area of more severe atopic dermatitis characterized by a dark grey brown, markedly lichenified skin with prominent scale. Four frank excorations are demonstrable. (Persons with atopic dermatitis almost always itch). In the center of the photograph are 2 MCV papules around which are clear zones of normal skin. Hence the anti-inflammatory effect to MCV is sufficiently powerful to suppress even severely dermatitic atopic skin.

The zone of inhibition around each MCV papule may be viewed as analogous to the zone of inhibition around a penicillin disk on an agar plate streaked with Streptococci. The therapeutic implications are also analogous.

Figure 5A:
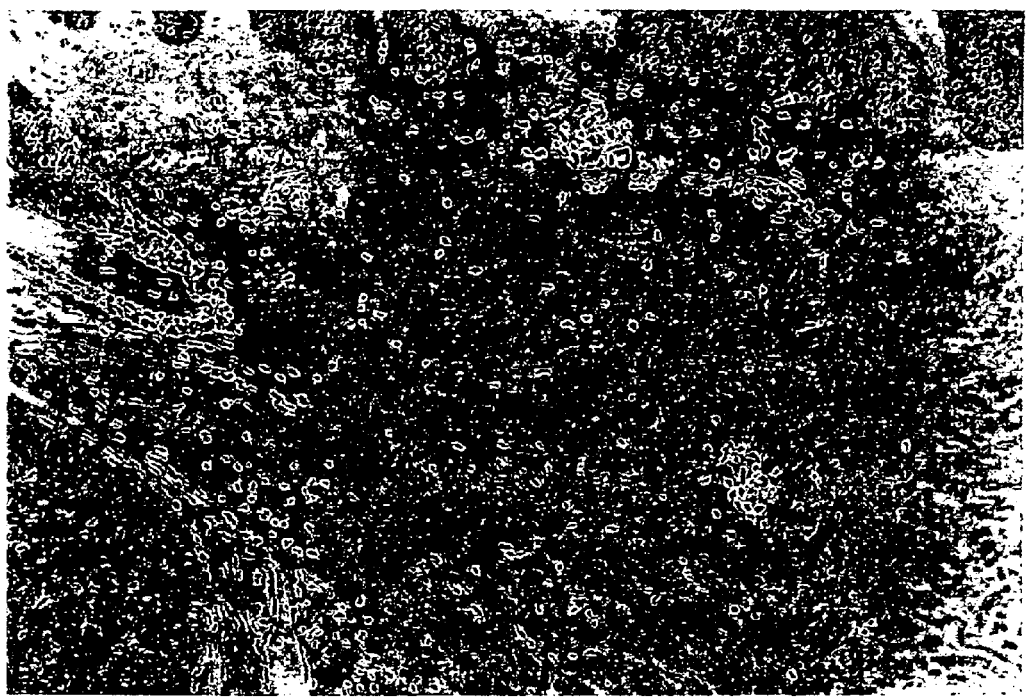
FIG. 5A illustrates the microscopically demonstrable inhibitory effect of MCV upon a field of AD.
Figure 5B:
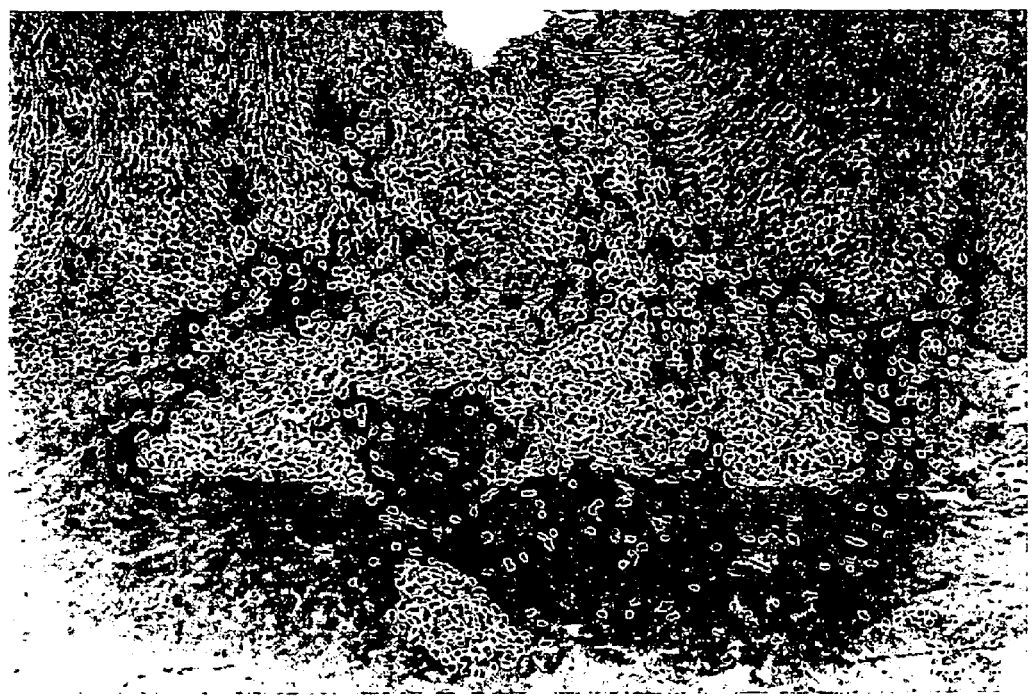
FIG. 5B illustrates the appearance of AD in the same patient shown in FIG. 5A at the same time at a site of AD remote from MCV.

FIGS. 5A–5B illustrates the microscopically demonstrable inhibitory effect of MCV upon a field of AD.

The photomicrograft of the biopsy depicted in FIG. 5A was taken from an area of atopic dermatitis on the skin of PR immediately adjacent to a papule of Molluscum contagiosum virus (MCV). The edge of the papule is seen on the lower left, and within the lower spinous cell layer of the papule, the cytoplasm of the keratinocytes contains Molluscum bodies, visible on light microscopy as deposits of eosinophilic amorphous material. The top of the photomicrograph shows the base of the adjacent epidermis. Moderate numbers of fibroblasts are found in a modified connective tissue around the Molluscum papule. A paucity of mononuclear cells is seen around small blood vessels of the superficial dermal plexus. There is a mild to moderate acanthosis, seen here in the lower part of the epidermis. There is scant inflammatory infiltrate within the connective tissue in the region of the Molluscum papule, extending far laterally into the papillary and reticular parts of the dermis. The lack of inflammation in the dermis adjacent to the Molluscum papule resembles the milieu characteristic of normal skin. (H&E, 100).

The photomicrograft of the biopsy depicted in FIG. 5B was taken concurrently (the same date and time) from similar area of atopic dermatitis on the skin of PR remote from the Molluscum papule shown in FIG. 5A. The top of the photomicrograph shows a markedly acanthotic epidermis with a central adherent crust denoting a site of excoriation, due to the incessant itching characteristic of atopic dermatitis. The itching, in turn, is secondary to inflammatory mediators of diverse origin-many of which are the products of the inflammatory cells which infiltrate the skin of patients with atopic dermatitis. The moderately dense, predominantly lymphohistiocytic infiltrate is seen here not only around the blood vessels of the superficial plexus, but also around vessels of the upper reticular dermis serving that plexus and around vessels of the papillae. The infiltrate of inflammatory cells extends into the intersitium. Lymphocytic exocytosis is also present. (H&E, 100×). With further magnification, eosinophils can also be seen within the inflammatory infiltrate on this photomicrograph.

While the present invention is disclosed by reference to the preferred embodiments and examples detailed above, it is to be understood that these examples are intended in an illustrative rather than limiting sense, as it is contemplated that modifications and combinations will readily occur to those skilled in the art, which modifications and combinations will be within the spirit of the invention and the scope of the appended claims.

What is claimed is:

1. A method for treating a patient having atopic dermatitis, comprising:
administering to a patient having atopic dermatitis a therapeutically effective amount of a composition comprising a Molluscum Contagiosum viral protein (MC148P) which possesses atopic dermatitis inhibiting activity.

2. The method according to claim 1, wherein the MC148P protein is selected from the group consisting of MC148P1, MC148P2, MC148P3 and fragments, variants, analogs, and derivatives of MC148P1, MC148P2, and MC148P3 which possess atopic dermatitis inhibiting activity.

3. The method according to claim 1, wherein administering the composition includes topically applying the composition.

4. The method according to claim 1, wherein administering the composition includes injecting the composition.

5. The method according to claim 1, wherein administering the composition includes iontophoresis.

6. The method according to claim 1, wherein administering the composition includes electroporation.

7. The method according to claim 1, wherein the composition includes a dimethyl sulfoxide carrier.

8. The method according to claim 1, wherein the composition includes an azone carrier.

9. The method according to claim 1, wherein the composition includes a liposomal carrier.

10. The method according to claim 1, wherein the composition is delivered locally to an area where atopic dermatitis is believed to be present.

11. The method according to claim 1 the composition is delivered to a patient with an atopic disease or allergic skin disorder.

12. A kit for treating an inflammatory skin disease, comprising:
multiple separately packaged portions of a composition adapted for treating atopic dermatitis comprising a Molluscum Contagiosum Viral protein (MC148P) which possesses atopic dermatitis inhibiting activity.

13. The kit according to claim 12, wherein the MC148P is selected from the group consisting of MC148P1, MC148P2, MC148P3 and fragments, variants, analogs, and derivatives of MC148P1, MC148P2, and MC148P3 which possess atopic dermatitis inhibiting activity.

14. The kit according to claim 12, wherein the kit further includes
instructions teaching administration of the composition to a patient having atopic dermatitis.

15. The kit according to claim 13, wherein the instructions teach locally delivering the composition to an area adjacent where atopic dermatitis is believed to be present.

16. The kit according to claim 13, wherein the instructions teach topically applying the composition.

17. The kit according to claim 13, wherein the instructions teach injecting the composition.

18. The kit according to claim 13, wherein the instructions teach administering the composition through iontophoresis and/or electroporation.

19. The kit according to claim 11, wherein the composition includes a dimethyl sulfoxide carrier.

20. The kit according to claim 11, wherein the composition includes an azone carrier.

* * * * *

UNITED STATES PATENT AND TRADEMARK OFFICE
CERTIFICATE OF CORRECTION

PATENT NO. : 6,838,429 B2
DATED : January 4, 2005
INVENTOR(S) : Paslin

It is certified that error appears in the above-identified patent and that said Letters Patent is hereby corrected as shown below:

Column 1,
Line 61, delete "trichopyton" and insert -- trichophyton --;

Column 2,
Line 64, delete "ajar" and insert -- a jar --;

Column 3,
Line 56, delete "infection any" and insert -- infection without any --;
Line 57, delete "viewing micrographs" and insert -- viewing photographs --;

Column 4,
Line 19, delete "proteins to share" and insert -- protein share --;
Line 21, delete "Buget" and insert -- Bugert --;

Column 5,
Line 49, delete "α-sheets" and insert -- α-helices --;

Column 8,
Line 13, delete "enhances" and insert -- enhancers --.

Signed and Sealed this

Tenth Day of May, 2005

JON W. DUDAS
*Director of the United States Patent and Trademark Office*